United States Patent
Fischell et al.

(10) Patent No.: US 8,535,294 B2
(45) Date of Patent: Sep. 17, 2013

(54) CAROTID SHEATH WITH FLEXIBLE DISTAL SECTION

(75) Inventors: Robert E. Fischell, Dayton, MD (US); Timothy J. Lynch, Palm Harbor, FL (US); Tim A. Fischell, Kalamazoo, MI (US)

(73) Assignee: Fischell Innovations LLC, Fair Haven, NJ (US)

( * ) Notice: Subject to any disclaimer, the term of this patent is extended or adjusted under 35 U.S.C. 154(b) by 0 days.

(21) Appl. No.: 13/150,308

(22) Filed: Jun. 1, 2011

(65) Prior Publication Data

US 2012/0310212 A1 Dec. 6, 2012

(51) Int. Cl.
*A61M 25/00* (2006.01)
(52) U.S. Cl.
USPC ............ 604/526; 604/524; 604/525; 604/529
(58) Field of Classification Search
USPC .......................................... 604/525–527, 529
See application file for complete search history.

(56) References Cited

U.S. PATENT DOCUMENTS

| | | | |
|---|---|---|---|
| 4,224,937 A | 9/1980 | Gordon | |
| 4,362,156 A | 12/1982 | Feller, Jr. et al. | |
| 4,705,511 A | 11/1987 | Kocak | |
| 4,862,891 A | 9/1989 | Smith | |
| 4,997,421 A | 3/1991 | Palsrok et al. | |
| 5,069,674 A | 12/1991 | Fearnot et al. | |
| 5,180,376 A | 1/1993 | Fischell | |
| 5,324,262 A | 6/1994 | Fischell et al. | |
| 5,360,432 A | 11/1994 | Shturman | |
| 5,413,562 A | 5/1995 | Swauger | |
| 5,423,774 A | 6/1995 | Fischell et al. | |
| 5,454,795 A | 10/1995 | Samson | |
| 5,484,425 A | 1/1996 | Fischell et al. | |
| 5,496,344 A | 3/1996 | Kanesaka et al. | |
| 5,514,236 A | 5/1996 | Avellanet et al. | |
| 5,531,721 A | 7/1996 | Pepin et al. | |
| 5,630,806 A | 5/1997 | Inagaki et al. | |
| 5,700,253 A | 12/1997 | Parker | |
| 5,702,373 A | 12/1997 | Samson | |
| 5,704,926 A | 1/1998 | Sutton | |

(Continued)

FOREIGN PATENT DOCUMENTS

WO    WO2009045276    4/2009

OTHER PUBLICATIONS

Restriction Requirement dated Nov. 18, 2011 for U.S. Appl. No. 13/032,876.
Office Action dated Dec. 8, 2011 for U.S. Appl. No. 13/032,876.

(Continued)

*Primary Examiner* — Emily Schmidt
(74) *Attorney, Agent, or Firm* — Stoel Rives LLP

(57) ABSTRACT

The present invention is a carotid sheath that has a proximal portion that is stiffer than the distal portion of the sheath as a result of the proximal portion having a higher durometer of the outer plastic coating of the sheath's proximal portion with a lower durometer for the plastic coating on the more flexible distal portion of the sheath. Another means to increase the flexibility of the sheath's distal portion compared to a stiffer proximal portion is by having a slightly smaller outside diameter for the outer plastic coating of the distal portion of the sheath. A more flexible distal portion of the sheath allows easier access for angiography, angioplasty or stenting when the sheath is used to access the tortuous path encountered when entering the carotid arteries.

11 Claims, 2 Drawing Sheets

(56) References Cited

U.S. PATENT DOCUMENTS

| | | |
|---|---|---|
| 5,796,044 A | 8/1998 | Cobian et al. |
| 5,827,230 A | 10/1998 | Bierman |
| 5,827,239 A | 10/1998 | Dillon et al. |
| 5,863,366 A | 1/1999 | Snow |
| 5,879,499 A | 3/1999 | Corvi |
| 5,927,345 A | 7/1999 | Samson |
| 5,944,697 A | 8/1999 | Biche |
| 5,947,940 A * | 9/1999 | Beisel .......................... 604/526 |
| 5,976,120 A * | 11/1999 | Chow et al. .................. 604/525 |
| 6,152,912 A | 11/2000 | Jansen et al. |
| 6,165,163 A * | 12/2000 | Chien et al. .................. 604/523 |
| 6,338,725 B1 | 1/2002 | Hermann et al. |
| 6,533,770 B1 | 3/2003 | Lepulu et al. |
| 6,863,674 B2 | 3/2005 | Kasahara et al. |
| 6,939,337 B2 | 9/2005 | Parker et al. |
| 7,083,588 B1 * | 8/2006 | Shmulewitz et al. ............ 604/8 |
| 7,320,697 B2 | 1/2008 | Demond et al. |
| 7,331,966 B2 | 2/2008 | Soma et al. |
| 7,438,712 B2 | 10/2008 | Chouinard |
| 7,618,430 B2 | 11/2009 | Scheib |
| 7,655,021 B2 | 2/2010 | Brasington et al. |
| 7,815,762 B2 | 10/2010 | Lentz et al. |
| 7,905,877 B1 | 3/2011 | Jimenez et al. |
| 8,034,045 B1 | 10/2011 | Lyons |
| 8,262,625 B1 | 9/2012 | Fischell et al. |
| 2001/0010247 A1 | 8/2001 | Snow |
| 2001/0044633 A1 | 11/2001 | Klint |
| 2002/0169377 A1 | 11/2002 | Khairkhahan et al. |
| 2003/0093060 A1 | 5/2003 | Kempf |
| 2003/0225365 A1 | 12/2003 | Greff et al. |
| 2003/0229313 A1 | 12/2003 | Bierman |
| 2004/0010243 A1 | 1/2004 | Klint |
| 2004/0116960 A1 | 6/2004 | Demond et al. |
| 2004/0153049 A1 | 8/2004 | Hewitt et al. |
| 2004/0236346 A1 | 11/2004 | Parker |
| 2005/0021022 A1 | 1/2005 | Sturm et al. |
| 2005/0060017 A1 * | 3/2005 | Fischell et al. ................ 623/1.11 |
| 2005/0149060 A1 * | 7/2005 | Thorstenson et al. ........ 606/108 |
| 2005/0228479 A1 | 10/2005 | Pavcnik et al. |
| 2006/0064054 A1 | 3/2006 | Sakakine et al. |
| 2006/0089618 A1 | 4/2006 | McFerran et al. |
| 2006/0095050 A1 | 5/2006 | Hartley et al. |
| 2006/0155302 A1 | 7/2006 | Sisken et al. |
| 2007/0066958 A1 | 3/2007 | Wright et al. |
| 2007/0118207 A1 | 5/2007 | Amplatz et al. |
| 2007/0185521 A1 | 8/2007 | Bue et al. |
| 2007/0219500 A1 | 9/2007 | Wright et al. |
| 2008/0051758 A1 | 2/2008 | Rioux et al. |
| 2008/0097516 A1 | 4/2008 | Chang et al. |
| 2009/0018525 A1 | 1/2009 | Waite et al. |
| 2009/0054845 A1 | 2/2009 | Puhasmagi et al. |
| 2009/0157162 A1 | 6/2009 | Chow et al. |
| 2009/0234295 A1 | 9/2009 | Lampropoulos et al. |
| 2009/0240202 A1 | 9/2009 | Drasler et al. |
| 2009/0306591 A1 | 12/2009 | Amisar et al. |
| 2009/0306603 A1 | 12/2009 | Bierman et al. |
| 2010/0016837 A1 | 1/2010 | Howat |
| 2010/0049168 A1 | 2/2010 | Parker et al. |
| 2011/0160702 A1 | 6/2011 | Jimenez et al. |
| 2011/0245775 A1 * | 10/2011 | Tekulve ........................ 604/171 |
| 2012/0215174 A1 | 8/2012 | Fischell et al. |
| 2012/0265282 A1 | 10/2012 | Fischell et al. |

OTHER PUBLICATIONS

Office Action dated Mar. 1, 2012 for U.S. Appl. No. 13/032,876.
Office Action dated May 25, 2012 for U.S. Appl. No. 13/032,876.
International Search Report and Written Opinion dated Aug. 7, 2012 for PCT/US2012/035268.
International Search Report and Written Opinion dated Sep. 24, 2012 for PCT/US2012/043243.
International Search Report and Written Opinion dated Nov. 8, 2012 for PCT/US2012/40391.
Notice of Allowance dated Oct. 16, 2012 for U.S. Appl. No. 13/032,876.
Office Action dated Mar. 19, 2013 for U.S. Appl. No. 13/085,951.
International Search Report and Written Opinion dated Apr. 25, 2013 for PCT/US2013/020941.
Office Action dated Jun. 3, 2013 for U.S. Appl. No. 13/349,060.
Notice of Allowance dated Jul. 26, 2013 for U.S. Appl. No. 13/431,526.
International Search Report and Written Opinion dated Jul. 18, 2013 for PCT/US2013/033840.

* cited by examiner

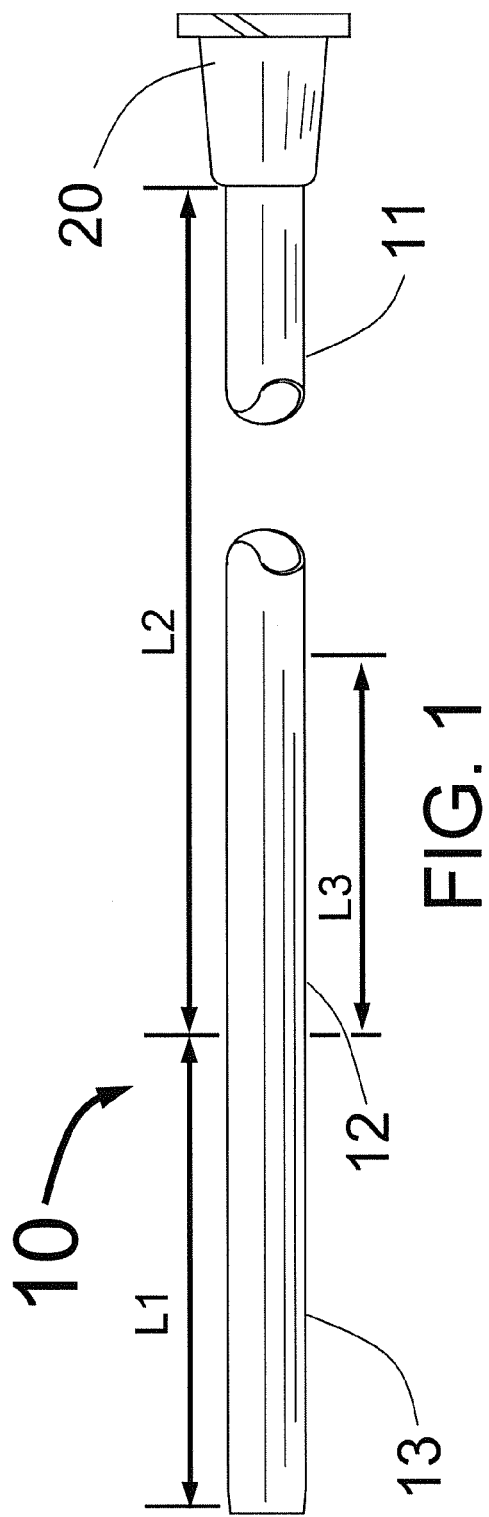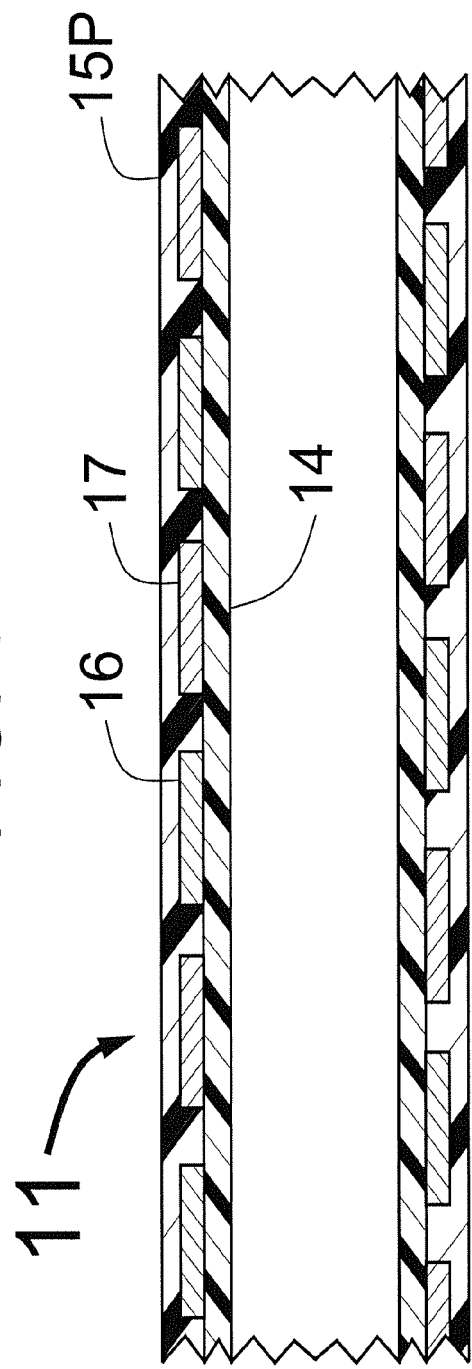

CAROTID SHEATH WITH FLEXIBLE DISTAL SECTION

FIELD OF USE

This invention is in the field of devices to assist in the placement of catheters through the skin to treat carotid artery obstructive disease.

BACKGROUND OF THE INVENTION

At the present time, physicians often treat carotid artery obstructive disease with the placement of a stent. This stent is typically placed in the internal carotid artery, in the common carotid artery, or spanning both arteries with the distal portion of the stent in the internal carotid artery and the proximal portion of the stent in the distal common carotid artery. The start of this procedure necessitates the placement of either a long sheath or a guiding catheter into the common carotid artery proximal to the carotid stenosis to be treated. The placement of such a sheath or guiding catheter can often be extremely challenging due to the tortuous course for access from the aortic arch into the common carotid artery. This is particularly an issue when accessing the right common carotid artery, which typically arises as a proximal branch from the inominate artery. Many different "tricks" are used to try to place relatively stiff sheaths and guiding catheters into the carotid circulation. One such "trick" is to have the sheath track over a "super-stiff" guidewire. Even with the best of equipment, it can be technically challenging, or even impossible to access the common carotid artery in order to stent a stenosis at that location when using any existing carotid sheath that has a uniform flexibility along its entire length. If stenting is not possible, then the more invasive and potentially life threatening procedure of a surgical endarterectomy may be required. Therefore, there is an important need for an improved carotid sheath that allows for more successful guidance through the tortuous vascular anatomy that is encountered when attempting to stent a stenosis in a carotid artery.

Another problem with current approach for carotid stenting is that it requires the placement of a relatively large sheath (typically 8 French) or a thick walled 7 French carotid sheath system to deliver the relatively high profile carotid stent delivery catheter. The use of these larger diameter sheaths can lead to an increased likelihood of vascular access bleeding after the sheath has been removed. In general, there is a relationship between the outer diameter of the inserted sheath and the risk of bleeding complications. Thus, sheaths with thinner walls would have a smaller outside diameter. This would decrease the size of the hole at the vascular entry site which would reduce the risk of serious bleeding complications.

SUMMARY OF THE INVENTION

A sheath diameter is typically expressed in FR (read "French"), which is the diameter of the sheath in millimeters divided by three. So a 6 FR sheath has a diameter of 2 mm. Using the currently available technology for carotid stenting, it is typical to use a relatively small sized (5 FR or 6 FR) sheath and diagnostic catheter (e.g., Simmons, or Headhunter, etc.) to access into the proximal common carotid artery. A relatively stiff (exchange length) guidewire is then placed through this 5 FR or 6 FR diagnostic catheter. The guidewire is then advanced through the common carotid artery, and distally into the external carotid artery to "anchor" this wire. Once the stiff guidewire is in place, it allows the exchange over this wire of a guiding catheter or a long carotid "guiding" sheath. For the purposes of this specification, we will refer to this guiding catheter or long carotid sheath merely as a "sheath" or a "carotid sheath."

The present invention is a thin-walled, flat wire reinforced sheath with a differential in sheath flexibility from the proximal portion to the distal portion of the sheath. Specifically, the carotid sheath described herein would have a greater stiffness along most of its proximal length and more flexibility in the distal portion of the sheath in order to enhance sheath tracking over a guidewire, a diagnostic catheter, or a dilator. At this time, there is no sheath that exists that has a comparatively long (about 75 cm) and stiff proximal portion to provide "pushability" combined with a comparatively short (about 15 cm) distal portion that is highly flexible to provide ready tracking through the highly curved vascular anatomy that must often be navigated in order to successfully place a stent in a carotid stenosis. Such a novel carotid sheath would make stenting of a carotid stenosis a more predictably successful procedure.

Another important aspect of the present invention is the construction of the tubular shaft of the sheath. Existing sheaths have a wall thickness that is typically greater than 13 mils where 1.0 mil=0.001 inch. By using a flat wire helical coil with a wire thickness of approximately 1 mil to 3 mils, which coil has a very thin coating of plastic placed onto its inner and outer surfaces, it is possible to reduce the wall thickness of the tubular shaft to less than 7 mils and preferably to around 5 mils. Such a novel construction would reduce the outside diameter of the introducer sheath by approximately one French size compared to existing sheaths. Such a reduction in the diameter of the sheath would be advantageous in reducing the risk of bleeding at the groin that sometimes occurs after removal of sheaths having a larger outside diameter. Any method to decrease the requirement for surgical repair and/or a blood transfusion often needed for a major bleeding complication would be highly advantageous for the patient and could significantly decrease the morbidity, mortality and cost associated with catheterization procedures.

The present invention also envisions that the shaft of the sheath could employ a thin-walled, flat wire helical coil to be fabricated from a shape memory alloy such as Nitinol to prevent the possibility of kinking of the tubular shaft of the introducer sheath. Still further the present invention envisions a shaft made from two to four separate helical metal coils, one of a cobalt chromium alloy (e.g.; the alloy L605) to enhance the strength and radiopacity of the shaft and the other coil(s) to be made from stainless steel for cost economy. This novel design would be very advantageous for providing a thin-walled shaft for the sheath that is also radiopaque and reasonably economical to build. It is also envisioned that just using one or more stainless steel and/or cobalt chromium alloy flat wires wound onto an inner layer of PTFE plastic and then coated in a plastic such as Pebax could be an excellent design. An important feature of any flat wire used for such a sheath is that they would be annealed to be either half hard or quite soft so as to more easily place the flat wires into the sheath shaft. Another novel design aspect is to have a differential in sheath flexibility with greater flexibility in the distal portion by either changing the durometer, or the thickness of the plastic components from the sheath's proximal portion to its distal portion (i.e., higher durometer or thicker in the proximal portion rather than distal portion) and/or changing the winding frequency of the helical coil of flat wire as one moves from proximal to distal end of the sheath, such that the distal portion of the sheath is more flexible and trackable than the proximal portion of the sheath.

Thus, one object of this invention is to use thin-walled flat wire within the sheath to decrease the outer diameter of the sheath, which decreases the size of the vascular entry hole and potentially reduces access site bleeding complications.

Another object of this invention is to create a carotid sheath that has a differential in sheath flexibility such that the distal portion of the sheath is more flexible than the proximal portion of the sheath which provides greater trackability of the distal portion of the sheath into the common carotid artery or any other target vessel requiring access for percutaneous intervention.

Still another object of the invention is to have a carotid sheath that is quite stiff for most of its proximal length to enhance its pushability with a distal portion that is much more flexible to enhance trackability and to ease its passage into the carotid arteries.

Still another object of the invention is to have a carotid sheath that has a proximal portion that is stiffer than the distal portion of the sheath as a result of the proximal portion having a higher durometer of the plastic on the outer layer of the sheath's proximal portion with a lower durometer for plastic covering on the more flexible distal portion of the sheath.

Still another object of the invention is to have a carotid sheath that has a proximal portion that is stiffer than the distal portion of the sheath as a result of the proximal portion having a slightly thicker outer coating of the plastic on the sheath's proximal portion with a thinner coating of plastic covering the more flexible distal portion of the sheath.

These and other objects and advantages of this invention will become obvious to a person of ordinary skill in this art upon reading the detailed description of this invention including the associated drawings as presented herein.

BRIEF DESCRIPTION OF THE DRAWINGS

FIG. 1 illustrates the present invention having a proximal portion with a length L2, the proximal portion being quite inflexible and a distal portion having a length L1 that is highly flexible.

FIG. 2 is a cross section of the carotid sheath showing the construction details for its proximal portion.

DETAILED DESCRIPTION OF THE INVENTION

Figure 3:
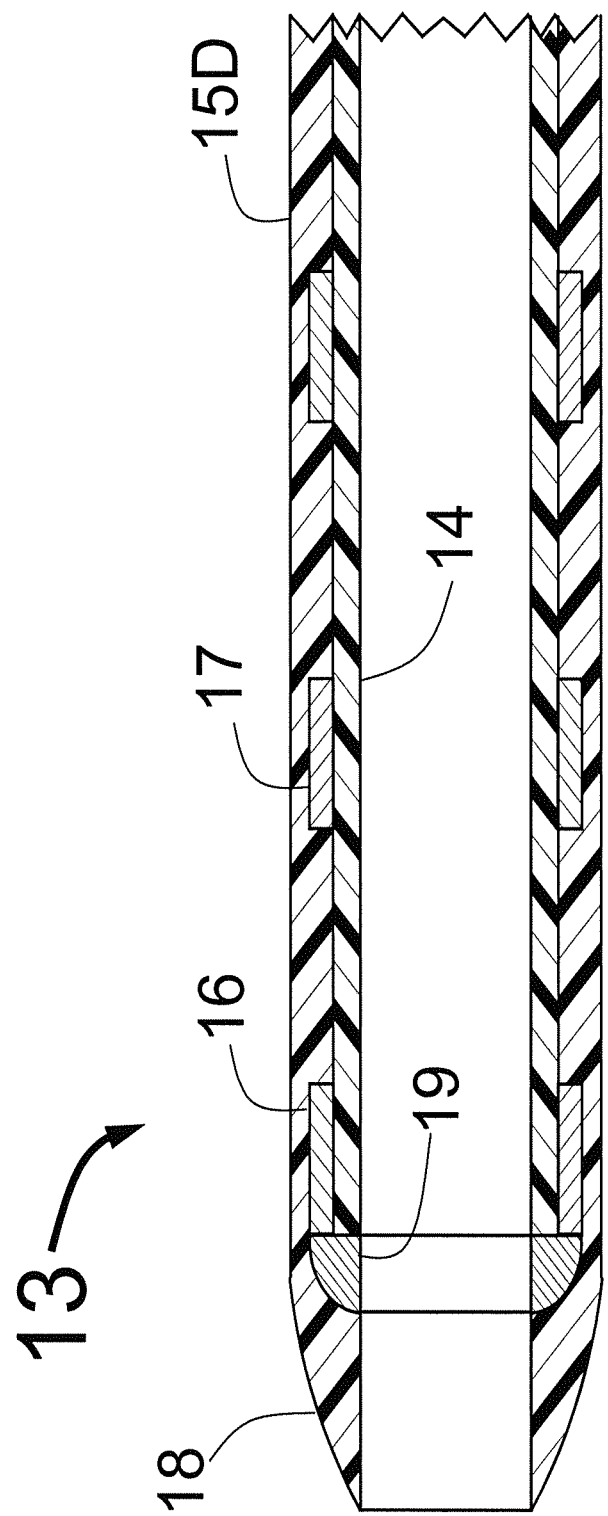
FIG. 3 is a cross section of a distal portion of the carotid sheath showing a means to increase the flexibility of the distal portion of the sheath.

FIG. 1 shows a sheath 10 having a comparatively flexible distal portion 13 having a length L1, a comparatively long and stiff proximal portion having a length L2 and a comparatively short transitional section 12 with length L3. Typical lengths L1, L2 and L3 would be L1=15±5 cm, L2=75±10 cm and L3=3±3 cm. The total length of the carotid sheath should be about 90 cm. FIG. 1 also shows a Luer fitting 20 at the proximal end of the sheath 10 which is typically used for injecting liquids through the sheath 10 or for connecting a Touhy-Borst fitting for performing carotid stenting. The Luer fitting 20 with the Touhy-Borst fitting also allows for the passage of a dilator. Though it is not shown in FIG. 1, the present invention also envisions having a Touhy-Borst fitting fixedly attached at the sheath's proximal end instead of the Luer fitting 20. This would save one step for the operator by not requiring the attachment of a separate Touhy-Borst fitting to the Luer fitting 20.

FIG. 2 shows a typical construction for the proximal portion 11 of the sheath 10. This portion of the sheath tubing would have an interior plastic coating 14 that would typically be formed from a lubricious plastic such as PTFE with a thickness that would typically be less than 1.0 mil, and an exterior plastic coating 15P on the proximal portion of the sheath 10 that would typically be formed from a Nylon type plastic such as Pebax with a thickness between 2 to 5 mils. Either or both coatings could be treated with a hydrophilic or other coating, to enhance their lubricity. The thickness of the Pebax could be thinned a bit in the distal portion, compared to the proximal portion of the sheath in order to enhance distal flexibility.

Between the interior and exterior plastic coatings 14 and 15P, 15D, an optimum sheath would utilize one or more several flat wire helical coils to create tubing that was non-kinking and also radiopaque. At least one helical coil 16 could be formed from a tough, radiopaque metal such as the cobalt chromium alloy L605. At least one additional helical coil 17 would be formed from stainless steel for additional non-kinking resistance and for cost economy. An optimum design might have as many as three separate helical coils of stainless steel and one helical coil of cobalt chromium.

It is also conceived to have just one to as many as four helical coils 17 formed from stainless steel. These flat wires would typically have a wall thickness of about 2.0±1.5 mils and a width that could be between 3 and 50 mils. An optimum flat wire would be approximately 2.0 mils thick and about 10 to 20 mils wide. The space between the wires that is occupied by the exterior plastic coating 15P, 15D would be approximately 10±5 mils wide for the comparatively stiff proximal portion 11 of the sheath 10. The inside diameter of the sheath would typically be formed to have a small clearance that allows for the passage of catheters that would have diameters between 4 FR and 9 FR. The outside diameter of the sheath would typically be approximately 1.0 FR size greater than the inside diameter of the sheath.

FIG. 3 is a cross section of the distal portion 13 of the sheath 10 showing a tapered radiopaque marker band 19 placed within a tapered tip 18. The distal portion 13 would typically have the same interior plastic coating 14 as is used for the proximal portion 11 of the sheath 10. The exterior plastic coating 15D for the flexible distal portion of the sheath would have a lower durometer as compared to the durometer for the proximal portion 11 of the sheath 10. The increased flexibility of the distal portion 13 can be achieved by a greater separation of the coils of the helical coils 16 and 17 as illustrated in FIG. 3. A greater separation of the flat wire helical coil 16, with the elimination of the helical coil 17 could also be used to provide the desired increased flexibility. Alternatively, the pitch angle of both helical coils 16 and 17 of the proximal portion 11 (as shown in FIG. 3) could be changed to provide increased separation of the coils as another means to provide the increased flexibility that is desired for the distal portion 13. It is certainly envisioned that the sheath 10 would have a single helical coil formed from flat wire with a tight spacing in the proximal portion 11, increased spacing through the transitional section 12 and a comparatively wide spacing of the flat wire helical coil for the sheath's distal portion 13. The separation between the flat wire coils for the distal portion 13 could be as great as 100±90 mils in order to achieve the desired degree of flexibility.

Still another means to improve the flexibility of the distal portion 13 would be to use an exterior plastic coating 15D on the distal portion 13 that has a decreased plastic durometer as compared to a higher durometer that would be used for the exterior plastic coating 15P of the proximal portion 11 of the sheath 10. For example, the harder plastic coating 15P could have a durometer of 75±10 and the softer plastic coating 15D could have a durometer of 45±10. Although it would be typical for the outside diameter of both plastic coatings 15P and 15D to have the same diameter, it is also envisioned that the proximal portion 13 could have a slightly smaller diameter to further improve the flexibility of the distal portion of the sheath 10. For example, the outer coating 15D of the distal portion 13 could have an outside diameter that is between 0.1 mil and 2 mils smaller than the outer diameter of the outer coating 15P of the proximal portion 11. Still further, it is envisioned that the transitional portion having a length L3 could have a variable durometer from being quite hard where it joins the proximal portion plastic coating 15P to a much softer durometer where it joins the distal portion plastic coating 15D.

What is claimed is:

1. A sheath for accessing a patient's vascular system, the sheath having a tubular shaft comprising an interior plastic coating, a wire layer, and an exterior plastic coating, the wire layer comprising at least two flat wire helical coils being made from different metals, wherein at least one flat wire comprises cobalt chromium, all the wires in the wire layer being wound such that all of the wires in the wire layer are non-overlapping and non-touching and wound in the same direction, where most of the length of the sheath is a proximal portion that is stiffer as to its bending characteristic as compared to a shorter distal portion of the sheath that has increased flexibility, the increased flexibility of the distal portion of the sheath being accomplished by having a greater separation between the helical coils in that distal portion as compared to a lesser separation between the helical coils at the longer, proximal portion of the sheath.

2. The sheath of claim 1 where the interior plastic coating comprises a lubricious plastic material, wherein the interior plastic coating and the exterior plastic coating are formed from different plastic materials and the wire layer is situated between the two plastic coatings.

3. The sheath of claim 1 where the length of the stiffer proximal portion is approximately 75±10 cm and the length of the distal portion of the sheath is approximately 15±10 cm.

4. The sheath of claim 1, further comprising a tapered distal end formed from a plastic material with a tapered radiopaque marker band situated within the tapered distal end.

5. The sheath of claim 2 where at least one flat wire between the plastic coatings is formed from stainless steel.

6. The sheath of claim 2 wherein the increased flexibility of the distal portion of the sheath is further achieved by a greater separation between the coils of at least one helical coil of flat wire that is situated between the interior plastic coating and the exterior plastic coating.

7. The sheath of claim 2 where the interior plastic coating is formed from PTFE or an equivalent lubricious plastic.

8. The sheath of claim 2 where the exterior plastic coating of the sheath comprises nylon.

9. The sheath of claim 2 where the exterior plastic coating of the sheath's distal portion is approximately 0.1 mil to as much as 2 mils smaller in outside diameter as compared to the outside diameter of the exterior plastic coating of the proximal portion of the sheath so as to improve the flexibility of the distal portion of the sheath compared to the flexibility of the proximal portion of the sheath.

10. The sheath of claim 2 where there is a transitional section of the sheath between the proximal portion and the distal portion, the transitional section having a tighter spacing between the coils of at least one flat wire helical coil near the proximal portion of the sheath and a greater separation between the coils of the at least one flat wire helical coil near the distal portion of the sheath.

11. The sheath of claim 2 where there is a transitional section of the sheath between the proximal portion and the distal portion, the transitional section having a higher durometer of the exterior plastic coating near the proximal portion of the sheath and a decreased durometer of the exterior plastic coating as it reaches the distal portion of the sheath.

* * * * *